United States Patent [19]

Chen

[11] 4,244,919
[45] Jan. 13, 1981

[54] SAMPLE DILUTING APPARATUS

[75] Inventor: Bu S. Chen, Miami, Fla.

[73] Assignee: Hyperion Incorporated, Miami, Fla.

[21] Appl. No.: 21,510

[22] Filed: Mar. 19, 1979

[51] Int. Cl.³ .............................................. G01N 1/14
[52] U.S. Cl. .................................. 422/100; 73/425.6; 222/70; 222/71; 422/63; 422/81; 422/103
[58] Field of Search ................... 422/63, 64, 100, 103, 422/81; 73/425.6, 425.4 R, 425.4 P, 423 A; 222/70, 71

[56] References Cited

U.S. PATENT DOCUMENTS

| | | | |
|---|---|---|---|
| 3,193,358 | 7/1965 | Baruch | 422/64 |
| 3,475,127 | 10/1969 | Gilford | 23/230 R |
| 3,475,130 | 10/1969 | Baruch | 422/64 |
| 3,482,451 | 12/1969 | Hrdina | 73/423 |
| 3,511,573 | 5/1970 | Isreeli | 422/82 |
| 3,655,094 | 4/1972 | Hobbs | 222/1 |
| 3,690,833 | 9/1972 | Ferrari | 23/230 R |
| 3,719,086 | 3/1973 | Bannister et al. | 73/423 A |
| 3,764,268 | 10/1973 | Kosowsky et al. | 422/64 |
| 3,982,667 | 9/1976 | Chen | 222/70 |

*Primary Examiner*—R. E. Serwin
*Attorney, Agent, or Firm*—Kenway & Jenney

[57] ABSTRACT

In the automatic liquid sample diluter disclosed herein, an excess of the sample liquid is drawn into the apparatus through a path which includes a conduit section of precisely predetermined volume. Valving means then switch this conduit section into the diluent discharge path so that accurate dilution ratios are obtained merely by controlling the discharged diluent volume.

13 Claims, 7 Drawing Figures

SAMPLE DILUTING APPARATUS

BACKGROUND OF THE INVENTION

This invention relates to an automatic diluter and more particularly to a diluter which permits precise dilution of sample fluids with repeatable accuracy.

Laboratory test equipment for performing qualitative or quantitative analyses on fluids, such as blood cell counts or hemoglobinometry on blood samples, require dilution of the sample fluids in ratios on the order of 101:1 to 500:1 or higher, accurate to precise tolerances, in order to insure accuracy of test results. Automatic diluters, which replace tedious manual dilution procedures, are well known in the prior art. U.S. Pat. Nos. 3,690,833; 3,764,268 and 3,982,667 illustrate examples of previously known automatic units. However, to deliver the precise dilution required, typical prior art diluters were dependent on the ability to control both the volume of the sample fluid and the correspondingly large volume of diluent at the moment of their initial injection into the apparatus. Possible volumetric errors inherent in the particular injection mechanism utilized could affect each of the independently injected quantities of fluids, resulting in a cumulatively large deviation from the desired dilution ratio. So, if calibration and operator errors are also taken into consideration, diluters based on such an operating principle would have four major sources of error inherently built in.

Another variable having an adverse effect on dilution accuracy is the presence of residual amounts of sample fluid in the diluter's sample inlet line, which can contaminate the particular sample being processed. Typically, prior sampler/diluters would have to perform a specific step in the operation directed solely to cleaning such residue from the system. U.S. Pat. No. 3,719,086 is illustrative of this approach.

An object of the present invention is to provide an automatic diluter which will deliver a constant volume of sample for dilution by a simple, inexpensive mechanism, free from cyclic volumetric errors and relatively immune to loss of accuracy with the passage of time.

Another object of the invention is to provide an automatic diluter which is simple to set up and adjust to yield accurate dilution ratios, and which presents fewer opportunities for operator error.

Still another object of the invention is to provide an automatic diluter which will remove sample residue from the sample inlet as a necessary consequence of the normal sample intake procedure and eliminate any superfluous intermediate cleaning step.

SUMMARY OF THE INVENTION

An automatic sample diluting apparatus in accordance with the present invention includes reciprocable sample and diluent pumps which are coupled for conjoint operation. It further includes a sample intake means, a diluent inlet connected to the diluent pump, and an output means through which sample and diluent are to be discharged. A sample volume defining conduit is provided, as is a bipartite valving means which engages both ends of this conduit. This valving means is capable of occupying two states, a first state in which the sample volume defining conduit is interposed between the sample intake means and the sample pump and a second state in which the conduit is interposed between the diluent pump and the output means. A timing means is provided which places the valving means in its first state when the pumps are drawing and in its second state when the pumps are discharging.

A particular embodiment of the present invention includes two reciprocating pumps, one for sample fluid intake, one for diluent intake, which draw in and expel their respective fluids through the internal piping of the apparatus. The pumps can be arranged so as to be driven simultaneously by a common drive mechanism, so that their intake and output strokes coincide. Additionally their respective displacements can be varied independently.

During the simultaneous intake strokes of the pumps, diluent is drawn into the diluter through a diluent inlet line, and a nominal volume of sample fluid is drawn in from its container by means of a conventional aspirating probe. The sample fills a section of tubing having a fixed constant internal volume, which has been interconnected between the sample pump and the sample probe by a set of valves attached to either end of the tubing. The tubing's internal volume now has defined accurately the volume of sample to which the diluent will be added.

As the pumps go into their output stroke, a timing mechanism simultaneously switches the valves to alternate positions, whereby the sample volume-defining tubing is interconnected between the diluent pump and the output of the diluter. The previously drawn-in diluent is forced through the tubing, pushing the entrapped sample ahead of it, until both the sample and the diluent are discharged together through the output. The dilution ratio of the now diluted sample can be measured and only the displacement of the diluent pump need be adjusted accordingly to achieve the proper result.

Any sample residue left inside the sample probe will be removed during the subsequent intake cycle of the diluter. As a stream of new sample enters the probe, its leading edge will push any residue ahead of it. Since the nominal volume of sample is larger than the volume of the sample volume-defining tubing, this contaminated leading edge will be excluded from the portion of sample which actually becomes diluted, and eventually will be discharged as waste.

BRIEF DESCRIPTION OF THE DRAWINGS

The apparatus will be described in detail with reference to the drawings in which.

DESCRIPTION OF THE PREFERRED EMBODIMENT

Figure 1:
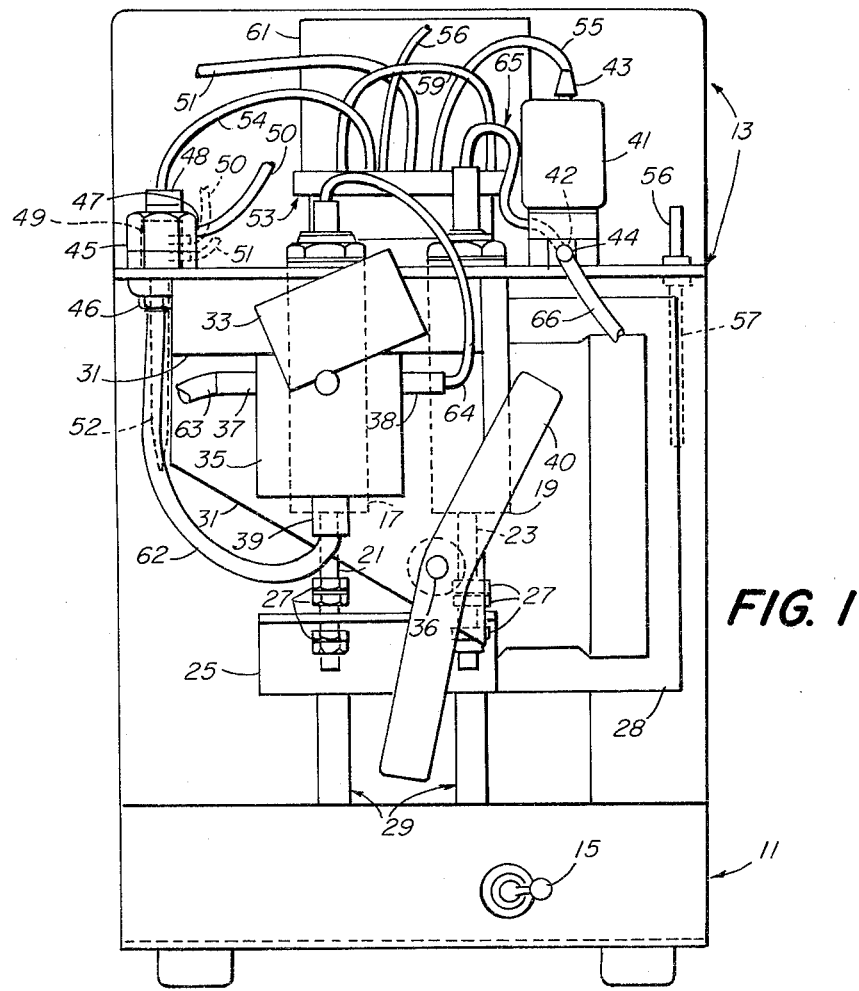
FIG. 1 is a rear view, in elevation, of an automatic diluter in accordance with the present invention, showing the general arrangement of the parts.

Referring now to FIG. 1, there is shown a rear elevation view of an automatic diluter in accordance with the present invention. A housing 11 and an L-shaped top plate 13 provides both a partial enclosure as well as mounting surfaces for the parts of the apparatus. A switch 15 turns the electrical power on to the apparatus, and is mounted on housing 11. A diluent cylinder 17 and a sample cylinder 19, which both are fastened to the underside of top plate 13, each contain a fluid-driving piston (not shown) whose downward and upward displacement within the cylinder alternately will create an intake and discharge reciprocal pumping action. Piston studs 21 and 23 are fixedly attached at one end to the diluent piston and the sample piston respectively, and project downwardly therefrom. The threaded bottom ends of studs 21 and 23 pass through clearance holes in a drive bar 25, and are loosely coupled to drive bar 25 by nuts 27. Drive bar 25 is rigidly attached to a drive plate 28, which plate can be driven upwardly and downwardly along guide rods 29, which guide rods are fastened at their bottom ends to housing 11 and at their top ends to top plate 13. This upward and downward motion of drive bar 25 moves studs 21 and 23 and their respective pistons in unison, producing simultaneous intakes and discharges in cylinders 17 and 19. The displacements of the diluent and sample pistons can be varied by adjusting nuts 27, which will change the vertical travel of studs 21 and 23. The driving mechanism for drive plate 28 will be described in detail hereinafter, in reference to FIG. 3.

A support plate 31, appearing in cross section as an inverted J, is attached to the underside of top plate 13. A microswitch 33 and a dual check valve 35 are mounted on plate 31 and gear motor shaft 36 extends through plate 31 as well. Check valve 35 has three access ports 37, 38, 39, and its internal structure permits fluid to flow from port 37 to port 38, but not in the reverse direction and from port 38 to port 39, but not in reverse. A lever arm 40 is adjustably fixed perpendicularly to the end of, and rotates with, shaft 36, and is positioned in such a way that both ends of lever arm 40 alternately make contact with microswitch 33.

A solenoid valve 41, which is attached to the top side of top plate 13, has three ports, 42,43,44. Solenoid valve 41 can be switched electrically from a state in which ports 42 and 43 are interconnected, to a second state in which ports 42 and 44 are interconnected.

A divider 45, which also is mounted on the top side of top plate 13, has a single input 46 but two outputs, a major output 47 and a minor output 48. Due to the design of divider 45, the fluid volume exiting through output 47 will be approximately double the fluid volume exiting through output 48.

A combining chamber 49, mounted to the top of plate 13, operates in a fashion opposite to divider 45, in that combining chamber 49 receives two fluid inputs, via tubings 50, 51, and discharges the combined fluids as a single output through a dispensing probe 52, which probe 52 is attached to and protrudes downwardly through top plate 13, externally to housing 11.

Figure 2:
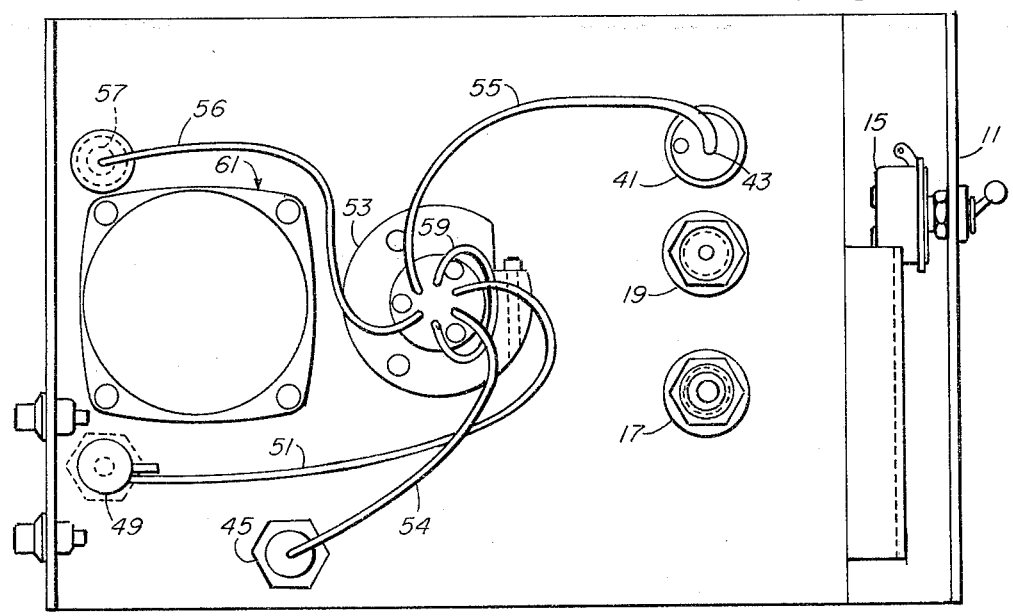
FIG. 2 is a top view of the diluter of FIG. 1, showing in particular the sample transfer valve and the tubing connections thereto.

A sample transfer valve 53, seated atop plate 13, has six access ports, which ports are interconnected with various components of the diluter by means of plastic tubing. FIG. 2 shows in detail the interconnetion of these various tubings with transfer valve 53. Tubing 54 links one of the ports to the minor output 48 of divider 45. Tubing 55 connects a second port to port 43 of solenoid 41. Tubing 51 joins a third port to combining chamber 49. Tubing 56 connects a fourth port to a sample intake probe 57, which probe 57 is mounted to the underside of top plate 13, and extends downwardly from plate 13, outside of housing 11. The last two ports of transfer valve 53 are joined together by a sample holding tube 59, which tube 59 has a defined constant internal volume. Transfer valve 53 can be switched mechanically by a reversible valve control motor 61, in a manner hereinafter described, between two alternate internal configurations, a first configuration in which tube 59 is interposed between tubings 55 and 56, and a second configuration in which tube 59 is interposed between tubings 51 and 54.

Again referring to FIG. 1, several other lengths of plastic tubing similarly interconnect other portions of the diluter apparatus. A diluent discharge tubing 62 joins port 39 of check valve 35 to input 46 of divider 45. A diluent inlet tubing 63 brings fresh diluent fluid from an external reservoir (not shown) into port 37 of check valve 35. Tubing 64 links port 38 of check valve 35 with diluent cylinder 17. Tubing 65 connects sample cylinder 19 with port 42 of solenoid valve 41. A waste discharge tubing 66 leads from port 44 of solenoid 41 to the exterior of the diluter. Tubing 50 joins combining chamber 49 with the major output 47 of divider 45.

Figure 3:
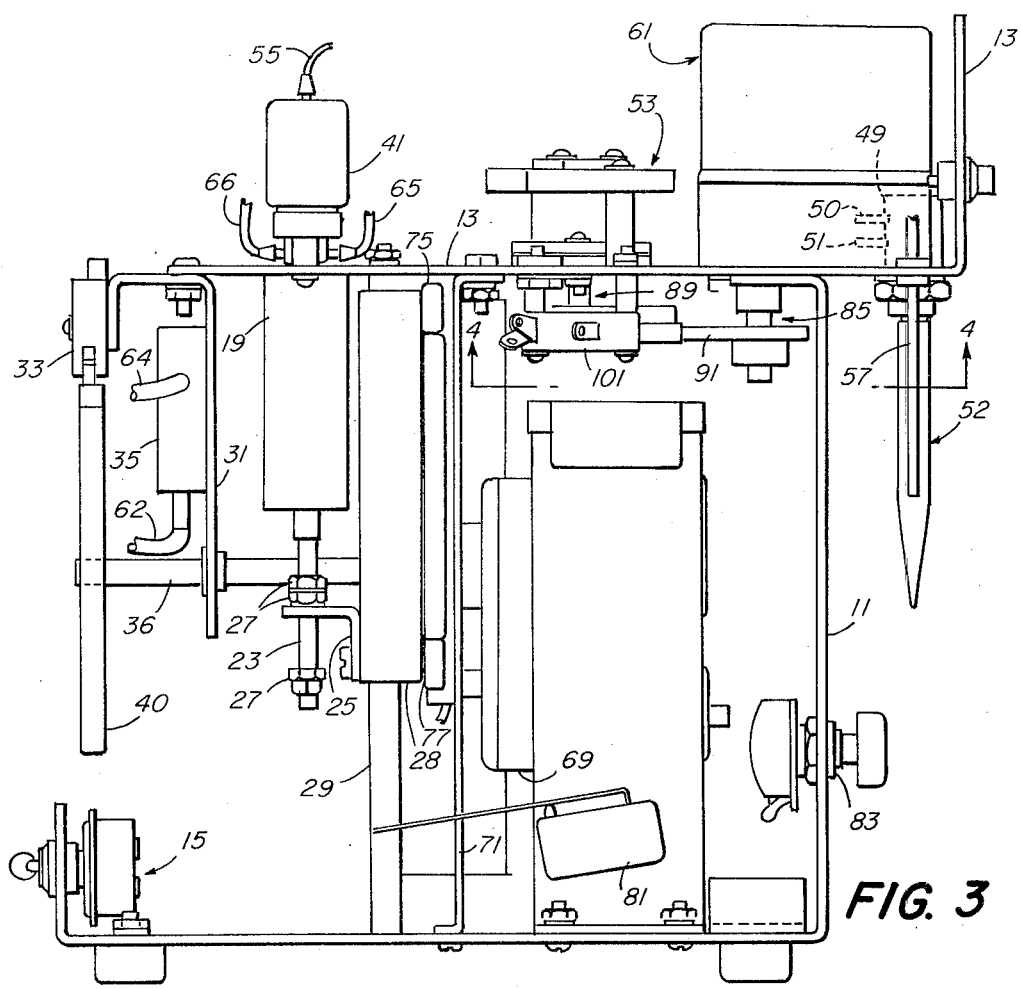
FIG. 3 is a side view, in elevation, of the automatic diluter of FIG. 1.

Referring now to FIG. 3, there is shown a side view, in elevation, of the apparatus. A vertical frame plate 71, attached at its bottom edge to housing 11 and at its top edge to top plate 13, provides a mounting surface for a gear motor 69. Gear motor shaft 36 extends through frame plate 71 and then continues through support plate 31 and is terminated by lever arm 40. A cam 73 is adjustably attached perpendicularly to shaft 37. A top cam follower 75 and a bottom cam follower 77 are rotatably fastened to, respectively, the top and bottom edges of drive plate 28. As shaft 36 and cam 73 rotate, cam followers 75 and 77 will ride along the edge surface of cam 73, and will raise and lower drive plate 28, and consequently drive bar 25, accordingly, along guide rods 29. A more detailed description of the cam and cam follower operation is contained in U.S. Pat. No. 3,655,094, and particularly in FIGS. 8 and 9 thereof, which patent hereby is incorporated by reference. Lever Arm 40 and cam 73 are designed and positioned whereby one end of arm 40 will contact microswitch 33 at the time of highest vertical position of drive bar 25, and the opposite end of arm 40 will contact microswitch 33 at the time of lowest vertical position of drive bar 25. As will be discussed with reference to FIG. 5, these cyclical contacts with microswitch 33 shut off gear motor 69. A microswitch 81, mounted on support plate 67, is positioned so as to be struck by drive plate 28 at the bottommost point of travel of plate 28, at the same time as microswitch 33 is being contacted by lever arm 40. A pushbutton start switch 83, mounted on the front of housing 11, turns on gear motor 69, in a manner described later. A footswitch, not shown, also can be provided to perform the same function.

Valve control motor shaft 85 extends downwardly from reversible valve control motor 61, through top plate 13, into the interior of housing 11. A valve lever assembly, indicated generally at 87, is engaged at one end to motor shaft 85 and at the other end to a valve shaft 89.

Figure 4:
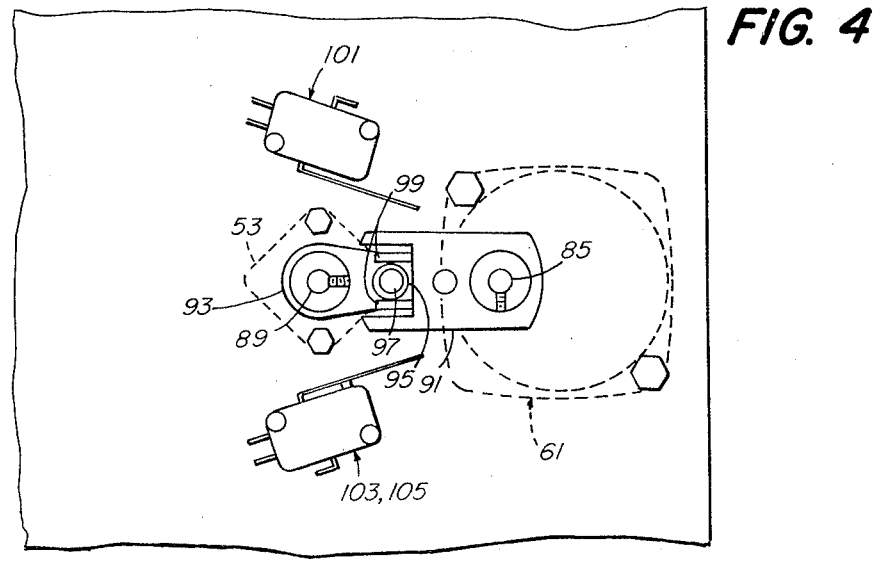
FIG. 4 is a detail view of the sample transfer valve and the associated switching mechanism therefor, taken along the line 4—4 of FIG. 3.

FIG. 4 shows a detail view of the sample transfer valve switching mechanism as viewed from the underside. Valve lever assembly 87 includes a lever arm 91 adjustably connected at one end to shaft 85, a control arm 93 adjustably connected at one end to switching shaft 89, a roller 95 rotatably attached to the opposite end of arm 93 by a pin 97, and bifurcated fingers 99, emanating from the opposite end of lever arm 91, which fingers tightly grip roller 95. As motor shaft 85 is rotated by valve control motor 61, lever arm 91 pivots accordingly. The coupling effected by the engagement of fingers 99 with roller 95 transmits this motion to control arm 93, and control arm 93 then turns shaft 89. This rotation of shaft 89 effects the previously described change of internal configurations within transfer valve 53. Motor 61 continues to run until lever arm 91 strikes either a microswitch 101 or the tandem-mounted combination of microswitches 103 and 105, depending upon the initial direction of travel of arm 91. Contact with either switch 101 or the switches 103,105 combination will shut off motor 61 as will be explained hereinafter.

Figure 5:
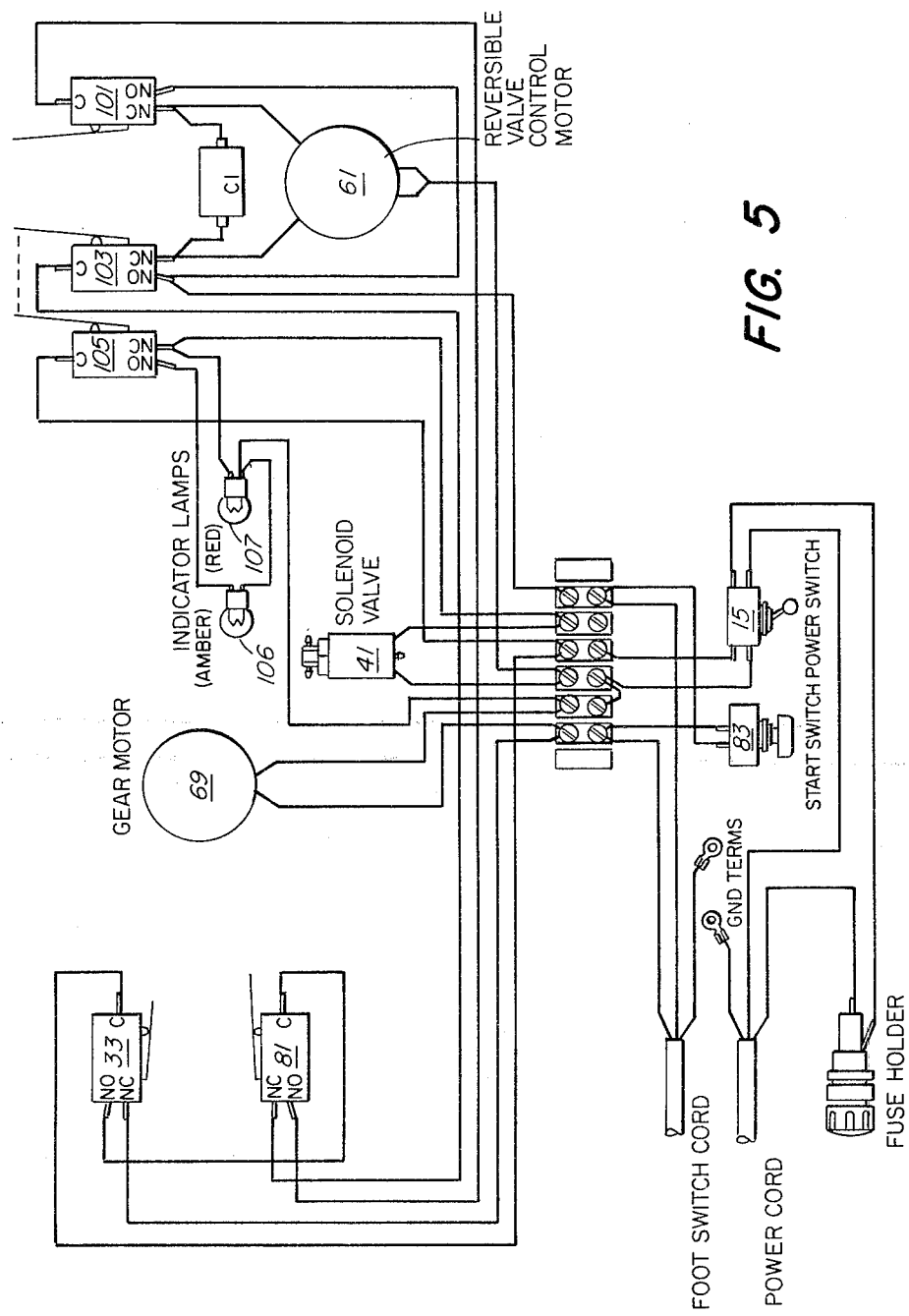
FIG. 5 is a schematic diagram of the electrical interconnections of the automatic diluter.

Referring now to FIG. 5, there is shown a schematic diagram of the electrical interconnections of the diluter. Switch 15 is the main power switch to the apparatus. Let us assume that at the time switch 15 is turned on, gear motor 69 is off, because microswitch 33 has been activated by being contacted by lever arm 40. Let us further assume that microswitch 81 is "off", indicating that drive plate 28 is not at the lowest point of travel, but rather is at the highest point. Activation of microswitch 33 provides power to valve control motor 61 through switches 81 and 103. The windings of motor 61 are wired to switch 103 such that motor 61 turns lever arm 91 toward switches 103 and 105. Motor 61 continues to turn until lever arm 91 strikes and activates the ganged switches 103 and 105. Switch 103 will shut off motor 61, and switch 105 simultaneously will deenergize solenoid valve 41 and light amber indicator lamp 106. Lamps 106 and 107, mounted appropriately on the exterior of the diluter apparatus, indicate the operating status of the diluter, with amber light 106 indicating that the diluter is in the intake portion of its cycle, red light 107 indicating the discharge portion of the cycle.

Gear motor 69 can be started by pushing in and holding switch 83, which bypasses switch 33. After shaft 36 has rotated several degrees, lever arm 40 will lose contact with switch 33, turning "off" switch 33, so that motor 69 will continue to move even if switch 83 is now released. Motor 69 will turn until the opposite end of drive arm 40 hits switch 33 and simultaneously drive plate 28 hits switch 81. Switch 33 again will turn off motor 69, and will supply power to reversible motor 61 through switches 81 and 101. Motor 61 now will turn lever arm 91 in the opposite direction because of the way in which Motor 61's windings are wired to switch 101, thereby removing arm 91 from contact with switches 103 and 105, which causes solenoid valve 41 to energize, lamp 106 to go out, and lamp 107 to light. Motor 61 will continue to turn until lever arm 91 strikes switch 101, again shutting off motor 61.

Pushing in and holding switch 83 for a second time will restart Motor 69 until the first end of lever arm 40 again contacts switch 33, which will bring the diluter back to the same state in which it was when power switch 15 was turned on initially.

Figure 6:
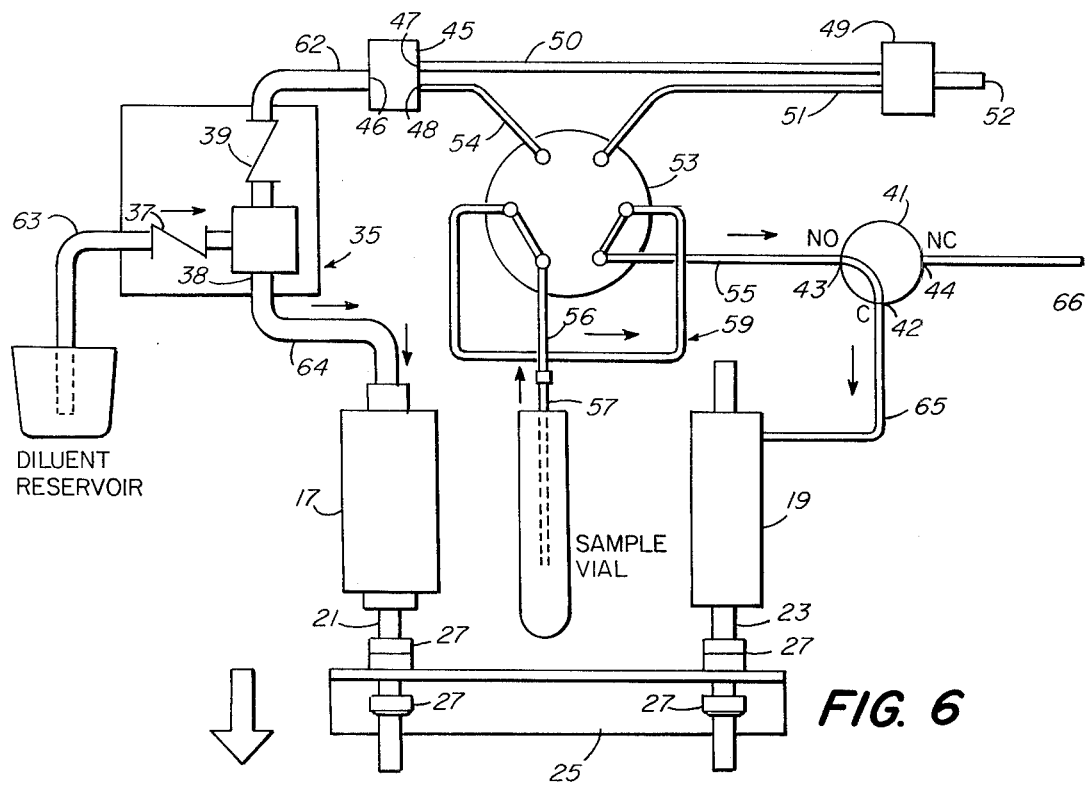
FIG. 6 is a schematic diagram depicting the flow of fluids through the automatic diluter during the intake portion of a typical dilution cycle.

Now, by referring to FIG. 6, the interactions of the various components will become evident as the intake portion of a typical cycle of the automatic diluter apparatus is described. At the start of the intake portion of the cycle, valve control motor 61 already has switched sample transfer valve 53 to its first internal configuration, whereby sample holding tube 59 is interposed between tubings 55 and 56. Solenoid valve 41 is deenergized, so that tubings 65 and 55 are interconnected. When start switch 83 is pressed, gear motor 69 starts, driving drive bar 25 downward. As the piston within sample cylinder 19 begins its downward movement, sample fluid is drawn in a continuous stream through probe 57, tubing 56, transfer valve 53, holding tube 59, tubing 55, solenoid valve 41, tubing 65 and toward, but not into sample cylinder 19. Similarly, under the influence of the downward-moving piston within diluent cylinder 17, diluent fluid is drawn in from its external reservoir by means of diluent inlet line 63, through port 37 of check valve 35 and tubing 64 toward diluent cylinder 17. Check valve 35 prevents diluent already present in discharge tubing 62 from a previous cycle from being drawn backwards into diluent cylinder 17. When the two pistons reach the lowest point in their travel and motor 69 stops, the intake portion of the cycle has been completed.

Figure 7:
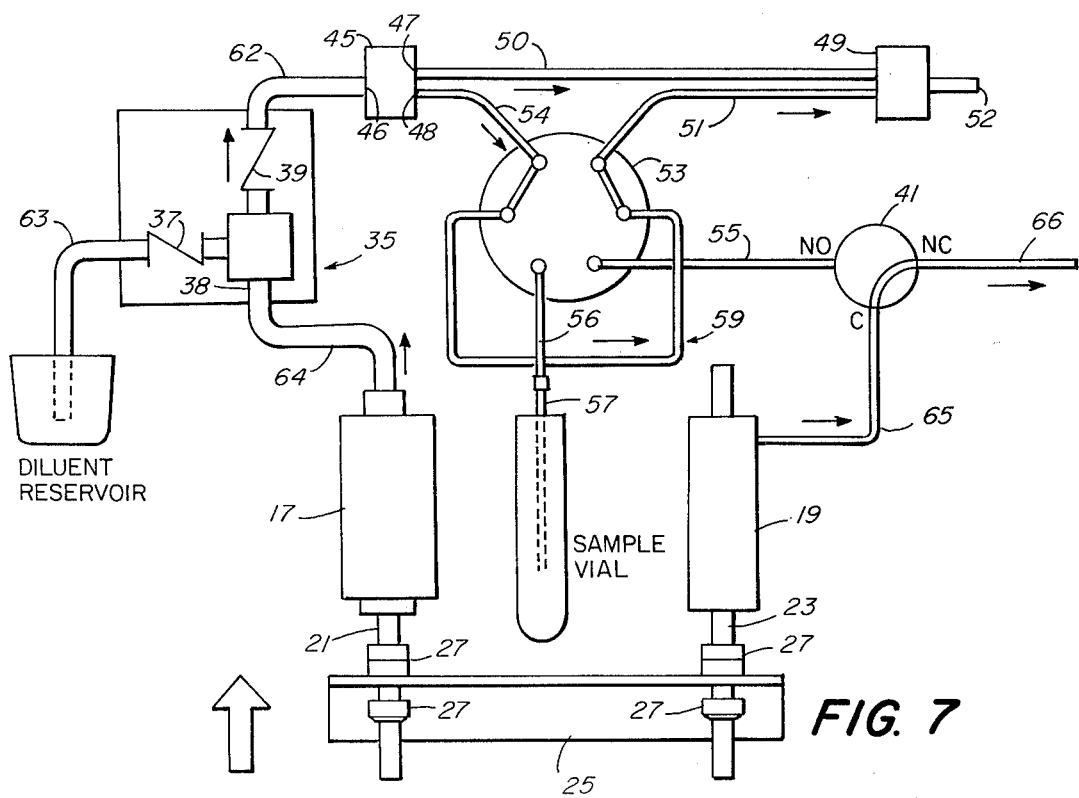
FIG. 7 is a schematic diagram depicting the flow of fluids through the automatic diluter during the discharge portion of a typical dilution cycle.

FIG. 7 next depicts the diluter components during the discharge portion of the cycle. Valve control motor 61 already has switched sample transfer valve 53 to its alternate position, whereby sample holding tube 59 is interposed between tubings 51 and 54. Solenoid valve 41 has been energized so as to disconnect tubing 65 from tubing 55 and reconnect tubing 65 to waste discharge tubing 66.

As the piston in diluent cylinder 17 starts moving upward, diluent in tubing 64 is forced through checkvalve 35 and discharge tubing 62 into divider 45. Check valve 35 prevents the diluent from reflowing into inlet line 63. Divider 45 splits the diluent flow into two streams, a larger stream which flows into tubing 50, and a smaller one which proceeds through tubing 54. This operation allows the major volume of diluent to bypass transfer valve 53 and holding tube 59, since typically the diluent volume will be several hundred times greater than the sample fluid volume being diluted, and it would be inefficient to pass this large volume through the necessarily smaller holding tube 59, as it may induce excessively high hydraulic pressure.

Diluent from line 54 then proceeds through transfer valve 53 into holding tube 59, forcing out the sample fluid contained therein, through tubing 51 into combining chamber 49. At this point the major stream of diluent is reintroduced via tubing 50 into combining chamber 49 and the dilution is accomplished. The final diluted sample then may be extracted by means of dispensing probe 52.

Simultaneously, excess sample fluid contained in tubing 65 is being forced out under the influence of the discharging sample cylinder 19, into solenoid valve 41. The excess sample proceeds into waste discharge tubing 66 and is discharged externally to the diluter, to vacate tubing 65 to accomodate new sample fluid during the next dilution cycle.

As can be seen from the foregoing disclosure, the aspirations of a precisely measured volume of sample fluid into the diluter is no longer a necessary starting point in the dilution process, and it can be eliminated as a potential major source of error. Accurate dilution is assured through the expedient of filling a length of tubing having a precisely determined constant internal volume with the sample fluid and then sealing off the ends of the tubing by a valve arrangement, making the sample fluid volume equivalent to the tubing's internal volume. Then, to insure achieving the proper dilution ratio, the volume of diluent to be added to this now well-defined volume of sample is adjusted until the end result shows repeatable accuracy. The constancy of the tubing's internal volume guarantees repeatability of a precise sample fluid volume, and typical minor volumetric changes in the larger diluent volume will have negligible effect on the desired dilution ratio.

As also can be seen from the foregoing disclosure, the problem of removal of sample residue from the lines is solved in a simple way, as a necessary outgrowth of the operating technique employed. Residue in the sample aspirating probe is purged by each subsequent aspiration, by the entry of the new sample fluid, whose leading edge pushes the residue ahead of it. Since a key feature of the present invention is the fact that more sample fluid is drawn into the apparatus at the start of each cycle than is needed to be diluted, the leading edge of the incoming sample flow will proceed completely through the length of tubing which defines the final sample volume, so that the residual sample will be excluded from the sample which ultimately becomes diluted.

As various changes could be made in the above constructions without departing from the scope of the invention, it should be understood that all matter contained in the above description or shown in the accompanying drawings shall be interpreted as illustrative and not in a limiting sense.

What is claimed is:

1. Automatic sample diluting apparatus comprising:
   a reciprocable sample pump;
   a reciprocable diluent pump, said pumps being coupled for conjoint operation;
   sample intake means;
   a diluent inlet;
   a sample volume defining conduit;
   output means through which sample and diluent are to be discharged;
   a bipartite valving means engaging both ends of said conduit, said valving means providing a first state in which said conduit is interposed between said intake means and said sample pump, and a second state in which said conduit is interposed between said diluent pump and said output means; and
   timing means for placing said valving means in said first state when said pumps are drawing and for placing said valving means in said second state when said pumps are discharging.

2. The apparatus as set forth in claim 1 wherein said pumps are piston types, in which the volume of each fluid pumped is determined by the diameter of a piston moving within a cylinder multiplied by the length of the stroke of the piston within that cylinder.

3. The apparatus as set forth in claim 1, wherein said sample volume defining conduit is a piece of tubing having the proper length and inside diameter to define the required volume.

4. The apparatus as set forth in claim 1, wherein said sample intake means in an aspirating-type probe.

5. The apparatus as set forth in claim 1, further comprising means, communicating with said sample pump, for evacuating excess sample fluid as waste when said sample pump is discharging.

6. The apparatus as set forth in claim 2, further comprising means for varying independently the lengths of the piston strokes so as to vary the volumes of fluids pumped.

7. The apparatus as set forth in claim 3, wherein said bipartite valving means has six access ports, two ports communicating with respective ends of said tubing, and one port each communicating with said sample intake means, said sample pump, said diluent pump and said output means, and wherein said valving means is mechanically rotatable to achieve the transition from first state to second state.

8. The apparatus as set forth in claim 7, further comprising a reversible motor, activated by said timing means, which motor rotates said valving means between states.

9. An automatic sample diluting apparatus, comprising:
   a reciprocating piston sample pump;
   a reciprocating piston diluent pump, said pumps being coupled for conjoint operation;
   a pump drive motor;
   means for independently adjusting the displacements of said pumps;
   a sample-aspirating probe;
   a diluent inlet;
   a diluent discharge;
   gating means to prevent communication between said diluent inlet and said diluent discharge;
   a divider, fed by said diluent discharge, to separate the diluent flow into major and minor components;
   a sample holding tube having a precisely defined constant internal volume;
   a combining chamber, fed by said major component of the diluent flow, through which chamber the sample and diluent are to be discharged;
   a sample transfer valve having a plurality of access ports, two of which ports communicate with opposite ends of said holding tube, which transfer valve can be switched mechanically between a first state in which said holding tube is interposed between said sample-aspirating probe and said sample pump, and a second state in which said holding tube is interposed between said minor component of the diluent flow and said combining chamber;
   a reversible valve control motor for switching said transfer valve;
   a waste discharge line;
   fluid switching means for alternately connecting said sample pump to either said sample transfer valve or said waste discharge line; and
   timing means for controlling the sequencing of the apparatus, whereby said transfer valve is in its first state and said sample pump is connected to said transfer valve when said pumps are drawing, so as to allow said holding tube to become filled with sample fluid, and whereby said transfer valve is in its second state and said sample pump is connected to said waste discharge line when said pumps are discharging, so as to allow diluent to pass through said holding tube and combine with the sample fluid, and to allow excess sample fluid to be evacuated through said waste discharge line.

10. The apparatus as set forth in claim 9, wherein said gating means is a check valve.

11. The apparatus as set forth in claim 9, wherein said fluid switching means is an electric solenoid valve.

12. The apparatus as set forth in claim 11, wherein said timing means includes:
first electrical switching means activated by said pumps at the times of transition from drawing to discharging and from discharging to drawing, said first switching means in turn energizing said valve control motor; and
second electrical switching means activated by said valve control motor, said second switching means both shutting off said valve control motor once said sample transfer valve has been switched between states, and also switching said fluid-switching means.

13. The apparatus as set forth in claim 12, wherein said first and second electrical switching means are mechanically actuated microswitches.

* * * * *